US009017985B2

(12) United States Patent
Kudla et al.

(10) Patent No.: US 9,017,985 B2
(45) Date of Patent: Apr. 28, 2015

(54) PHOTOSYNTHETIC MICROORGANISMS ENRICHED IN SELENIUM USING SELENOHYDROXY ACID COMPOUNDS, USED THEREOF IN NUTRITION, COSMETICS AND PHARMACY

(75) Inventors: Bernard Kudla, Les Molieres (FR); Frédéric De Baene, Chelles (FR); Marc Lange, Paris (FR)

(73) Assignee: Metabolium, Romainville (FR)

( * ) Notice: Subject to any disclaimer, the term of this patent is extended or adjusted under 35 U.S.C. 154(b) by 381 days.

(21) Appl. No.: 13/061,303

(22) PCT Filed: Aug. 28, 2009

(86) PCT No.: PCT/FR2009/001044
§ 371 (c)(1),
(2), (4) Date: Feb. 28, 2011

(87) PCT Pub. No.: WO2010/023384
PCT Pub. Date: Mar. 4, 2010

(65) Prior Publication Data
US 2011/0165658 A1    Jul. 7, 2011

(30) Foreign Application Priority Data

Aug. 29, 2008   (FR) ..................... 08 55827

(51) Int. Cl.

| | |
|---|---|
| A01G 33/00 | (2006.01) |
| A23J 1/09 | (2006.01) |
| A23J 3/20 | (2006.01) |
| A61K 38/00 | (2006.01) |
| C12N 1/00 | (2006.01) |
| C12N 1/12 | (2006.01) |
| C12N 1/20 | (2006.01) |
| A23L 1/30 | (2006.01) |
| A61K 8/58 | (2006.01) |
| A61K 8/99 | (2006.01) |
| A61Q 19/00 | (2006.01) |

(52) U.S. Cl.
CPC ................ *C12N 1/12* (2013.01); *A23L 1/3002* (2013.01); *A61K 8/58* (2013.01); *A61K 8/99* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 5,639,482 A | 6/1997 | Crary | |
| 6,197,295 B1 | 3/2001 | Hsia et al. | |
| 8,535,931 B2 | 9/2013 | Yadan et al. | |
| 2005/0089530 A1 | 4/2005 | Moesgaard et al. | |
| 2007/0053866 A1 | 3/2007 | Abou-Nemeh | |
| 2007/0258964 A1 | 11/2007 | Andreoni et al. | |
| 2008/0038367 A1* | 2/2008 | Saloum .................. | 424/617 |

FOREIGN PATENT DOCUMENTS

| | | |
|---|---|---|
| CN | 1283171 | 2/2001 |
| CN | 1302723 | 7/2001 |
| CN | 1778199 A | 5/2006 |
| CN | 1810161 A | 8/2006 |
| CN | 1817143 A | 8/2006 |
| DE | 198558670 A1 | 6/2000 |
| EP | 1 602 716 A1 | 12/2005 |
| GB | 2214928 A * | 9/1989 |
| GB | 2 216 421 A | 10/1989 |
| JP | 7300409 A | 11/1995 |
| KR | 950006950 B1 | 6/1995 |
| KR | 20040101145 A | 12/2004 |
| RU | 2209237 C2 | 7/2003 |
| TW | 565432 B | 12/2003 |
| WO | 03/078605 A1 | 9/2003 |
| WO | 2006008190 A2 | 1/2006 |
| WO | WO 2006008190 A2 * | 1/2006 |

OTHER PUBLICATIONS

Cases et.al, "Selenium from Selenium-Rich Spirulina is Less Bioavailable than Selenium from Sodium Selenite and Selenomethionine in Selenium-Deficient Rats," Journal of Nutrition, vol. 131, No. 9, pp. 2343-2350 (2001).*
Dumont et al., "Selenium speciation from food source to metabolites: a critical review," Analytical and Bioanalytical Chemistry, vol. 385, pp. 1304-1323; (2006).*
Schrauzer, G.N., "Commentary: Nutritional Selenium Supplements: Product Types, Quality, and Safety," Journal of the American College of Nutrition, vol. 20, No. 1, pp. 1-4; (2001).*
Douskova I. et al., "Scenedesmus quadricauda—A promising microorganism for selenium-enriched algal biomass production", Poster at Symposium for European Freshwater Sciences SEFS-5, Palermo Jul. 8-13, 2007, XP 55016178, extracted from the internet at: http//www.effsonline.org/index/sefsfsefs5/papers/contentParagraph/0114/document/Douskova.pdf (extracted on Jan. 11, 2012).
Besser, John M. et al., Bioacculmulation of organic and inorganic selenium in a laboratory food chain, Environmental Toxicology and Chemistry, vol. 12, 1993, pp. 57-72.
Cases, et al., "Selenium from selenium-rich spirulina is less bioavailable than selenium from sodium selenite and selenomethionine selenium-deficient rats", Journal of Nutrition, XP002526985, Sep. 2001, pp. 2343-2350, vol. 131, No. 9.
Larsen, et al., "Speciation of selenoamino acids, selenonium ions and inorganic selenium by ion exchange HPLC with mass spectrometric detection and its application to yeast and algae", Journal of Analytical Atomic Spectrometry, XP002526986, Dec. 2001, pp. 1403-1408, vol. 16, No. 12.
De Souza, et al., "Selenium assimilation and volatilization from dimethylselenoniopropionate by Indian mustard", Plant Physiology, XP002526987, Apr. 2000, vol. 122, No. 4.
Cases et al., Assessment of Selenium Bioavailability from High-Selenium Spirulina Subfractions in Selenium-Deficient Rats, J. Agric. Food Chem., 50:3867-3873 (2002).

(Continued)

*Primary Examiner* — Cherie M Stanfield
*Assistant Examiner* — Paul D. Pyla
(74) *Attorney, Agent, or Firm* — Browdy and Neimark, PLLC

(57) ABSTRACT

The invention relates to the enrichment of photosynthetic microorganisms in organic selenium using selenohydroxy acid compounds, in particular 2-hydroxy-4-methylselenobutanoic acid, in D or L form, or an enantiomer, salt or ester or amide derivative of these compounds, and also to the use of the microorganisms thus enriched in animal or human nutrition, in cosmetics or in pharmacy.

24 Claims, No Drawings

(56) References Cited

OTHER PUBLICATIONS

International Search Report issued in application No. PCT/EP2009/061165 on Oct. 9, 2009.

Alzate et al., "Comparison of Biotransformatino of Inorganic Selenium by *Lactobacillus* and *Saccharomyces* in Lactic Fermentation Process of Yogurt and Kefir," J. Agric. Food Chem ., 2008, pp. 8728-8736, vol. 56, No. 18.

Andreoni et al., "Selenite tolerance and accumulation in the *Lactobacillus* species," Annals of Microbiology, 2000, pp. 77-88, vol. 50.

Avoscan et al., "Selno-L-Methionine is the Predominant Organic Form of Selenium in *Cupriavidus metallidurans* CH34 Exposed to Selenite or Selenate," Appl. Environ. Microbiol., Sep. 2006, pp. 6414-6416, vol. 72, No. 9.

Calomme et al., "Seleno-*Lactobacillus*, An Organic Selenium Source," Biol. Trace Element Res., 1995, pp. 379-383, vol. 47.

Dumont et al., "Selenium speciation from food source to metabolites: a critical review," Anal. Bioanal. Chem., 2006, pp. 1304-1323, vol. 385.

Infante et al., "Selenium speciation analysis of selenium-enriched supplements by HPLC with ultrasonic nebulisation ICP-MS and electrospray MS/MS detection," J. Anal. At Spectrom., 2004, pp. 1529-1538, vol. 19.

McSheehy et al., "Determination of Methionine and Selenomethionine in Selenium-Enriched Yeast by Species-Specific Isotope Dilution with Liquid Chromatography—Mass Spectrometry and Inductively Coupled Plasma Mass Spectrometry Detection," Anal. Chem., Jan. 2005, pp. 344-349, vol. 77, No. 1.

Mester et al., "Certification of a new selenized yeast reference material (SELM-1) for methionine, selenomethinone and total selenium content and its use in an intercomparison exercise for quantifying these analytes," Anal. Bioanal. Chem., 2006, pp. 168-180, vol. 385.

Moller H., "The Chemistry of Natural and Synthetic Skin Barrier Lipids," Cosmetic Lipids and the Skin Barrier, Thomas Forster, Ed., 2002, pp. 1-3.

Mony et al., "RenalBioavailability of Selenium After Supplementation With Different Forms of Selenium: Ion Probe and Mass Spectrometry Study," J. Trace Elements in Experimental Med., 2000, pp. 367-380, vol. 13.

Muller et al., "The path of unspecific incorporation of selenium in *Escherichia coli*," Arch. Microbiol., 1997, pp. 421-427, vol. 168.

Schrauzer G.N., "Nutritional Selenium Supplements: Product Types, Quality, and Safety," Commentary, J. Amer. College of Nutrition, 2001, pp. 1-4, vol. 20, No. 1.

Von Stockhausen H.B., "Selenium in Total Parenteral Nutrition," Biolog. Trace Element Res., 1988, pp. 147-155, vol. 15.

Wendel A., "Biochemical Functions of Selenium," Phosphorus, Sulfur, and Silicon, 1992, pp. 405-415, vol. 67.

Xia et al., "Enriched Selenium and Its Effects on Growth and Biochemical Composition in *Lactobacillus bulgaricus*," J. Agric. Food Chem., 2007, pp. 2413-2417, vol. 55, No. 6.

* cited by examiner

PHOTOSYNTHETIC MICROORGANISMS ENRICHED IN SELENIUM USING SELENOHYDROXY ACID COMPOUNDS, USED THEREOF IN NUTRITION, COSMETICS AND PHARMACY

The invention relates to the enrichment of photosynthetic microorganisms in organic selenium, in particular using selenohydroxy acid compounds, and more particularly using 2-hydroxy-4-methylselenobutanoic acid, in (D,L) form, or of an enantiomer, salt or ester or amide derivative of this compound, and also to the use of the photosynthetic microorganisms thus enriched in animal or human nutrition, in cosmetics or in pharmacy.

Selenium is a micronutrient essential to humans and mammals in particular (Wendel, A.; *Phosphorus, Sulfur Silicon Relat Elem.*, 1992, 67, 1-4, 404-415). In particular, it participates, in the form of L(+)-selenocysteine or L(+)-selenomethionine (Muller, S. at al., *Arch. Microbiol.*, 1997, 168, 421), in the biosynthesis of selenoproteins such as glutathione peroxidase, thioredoxin reductase and selenoprotein P.

Selenium deficiencies have been reported in humans, in particular in the case of patients subjected to parenteral feeding over long periods of time (Von Stockhausen, H. B., *Biol. Trace Elem. Res.*, 1988, 15:147-155). A daily supplementation of 200 μg of selenium is considered to be safe and adequate for an adult human of average weight (Schnauzer, G. N., *J. Am. Col. Nutr.*, 2001, 20:1-14).

Selenium is found naturally, in two forms: organic and inorganic.

The inorganic compounds are most commonly salts such as sodium selenite or selenate. These compounds are very toxic to humans and most animals.

The organic compounds (organoselenium compounds) are represented in living organisms, in particular, by the amino acids L(+)-selenomethionine, L(+)-methylselenocysteine and L(+)-selenocysteine.

L(+)-Selenomethionine is the main source of organic selenium in humans and animals. However, humans and animals are autoxotrophic for this amino acid, which can be obtained only through the diet.

Selenium should therefore ideally be incorporated into food supplements aimed at treating or preventing a selenium deficiency, in this organic form.

It has thus been possible to demonstrate that supplementing the diet with L(+)-selenomethionine is much less toxic and provides better bioavailability than an intake in the form of sodium selenite (Mony, M. C. et al., *J. of Trace Elem. Exp. Med.*, 2000, 13:367-380).

Currently, metabolic pathways for selenium uptake by living organisms other than those using inorganic selenium, mainly in the form of sodium selenite, and selenomethionine, as substrates are unknown.

A suitable supply of organic selenium can be found in higher plants (wheat, maize, soya, in particular), in which more than 80% of the selenium is made up of L(+)-selenomethionine (Schnauzer, G. N., *J. Am. Coll. Nutrit.*, 2001, 20(1): 1-4). However, the selenium concentration in these plants is not sufficient to be able to readily, and less expensively, produce food additives.

One of the approaches explored for obtaining selenomethionine-rich compositions consists in enriching certain microorganisms in organic selenium using inorganic selenium. Once enriched, these microorganisms can be used as starting material for the preparation of food or cosmetic products.

Numerous publications describe, for example, the preparation of selenium-enriched yeasts, and more particularly the yeast *Saccharomyces cerevisiae* (Oh Tae-Kwang et al., patent KR950006950 of Jun. 26, 1995), for the purpose of using them as such or of incorporating them into food compositions (Moesgaard S. et al., patent DK200200408 of Sep. 16, 2003); or else of obtaining selenium-enriched derived products such as, for example, selenium-enriched bread (Wang Boaquan, patent CN 1817143 of Aug. 16, 2006), milk (Deng Chang-Yi, patent TW565432 of Dec. 11, 2003), eggs (Cui Li et al., patent CN1302723C of Mar. 7, 2007), chocolate (In Gyeong Suk et al., patent KR20040101145 of Nov. 8, 2004) or beer (Jakovleva L. G. et al., patent RU2209237 of Jul. 27, 2003). In the health foods sector, preparations containing selenium-enriched yeasts have also been proposed for pregnant women (Wang Weiyi, patent CN1778199 of May 31, 2006), or else for improving the intestinal microenvironment of hypoglycemic patients (Li Tao Zhao, patent CN1810161 of Aug. 2, 2006). In the dermocosmetics field, compositions containing selenium-enriched yeasts have been developed for the purpose of reducing hair loss (Kasik Heinz, patent DE19858670 of Jun. 21, 2000) or in the prevention of photoaging (Kawai Norihisa et al., patent JP07300409 of Nov. 14, 1995). Pharmaceutical preparations containing selenium-enriched yeasts have been used in the prevention and treatment of inflammatory pathological conditions such as retinopathies related to diabetes (Crary Ely J., patent U.S. Pat. No. 5,639,482 of Jun. 17, 1997), or which are cardiovascular (Nagy P. L. et al., patent HUT060436 of Sep. 28, 1992).

Bacteria, and more particularly probiotic bacteria, have themselves also been the subject of selenium enrichment (Calomme M. et al., *Biol. Trace Elem. Res.*, 1995, 47, 379-383). *Lactobacillus acidophilus*, but also *Lactobacillus reuteri, Lactobacillus ferintoshensis* and *Lactobacillus buchneri/parabuchneri* (Andreoni V. et al., patent U.S. Pat. No. 0,258,964) have been described as selenium-enriched food supplements. Mixtures of probiotics made up of yeasts and lactobacilli, for the purpose of reinforcing the immune system and resistance to diseases (Huang Kehe Qin, patent CN1283171C of Nov. 8, 2006) have been prepared.

However, in all these preparations, the selenium-enriched microorganisms are prepared from inorganic selenium only. Thus, the source of selenium most commonly used consists of sodium selenite or selenate solubilized in the culture media of the microorganisms. The microorganisms thus enriched, although having synthesized satisfactory amounts of organic selenium which can be assimilated by the human organism, often exhibit a high residual level of unconverted inorganic selenium, which can prove to be dangerous to the individual consuming same.

In a previous application published under WO 2006/008190, novel organic compounds of selenohydroxy acid type have been described as being able to serve as precursors for the synthesis of L(+)-selenomethionine in humans and animals.

Surprisingly, the applicant has noted that organic compounds of selenohydroxy acid type, such as those described in application WO 2006/008190, can be incorporated into culture media for enriching various photosynthetic microorganisms in organic selenium. The results obtained have revealed that these compounds make it possible to very efficiently enrich such micro-organisms, in particular in L(+)-selenomethionine, with a yield that is equivalent to, or even higher than, that obtained using the inorganic compounds normally used.

It has thus become apparent that the enrichment of photosynthetic microorganisms in organic selenium using organic compounds of selenohydroxy acid type makes it possible to produce organic selenium free of inorganic selenium, and also to solve the problems of toxicity related to the prior art methods.

The photosynthetic microorganisms thus enriched can be used directly in the food trade in the context of the prevention or treatment of selenium deficiencies, in particular for the purpose of producing pharmaceutical, nutritional or cosmetic products and compositions.

DETAILED DESCRIPTION OF THE INVENTION

The present application relates to the obtaining of photosynthetic microorganisms, that is to say of microorganisms, the growth of which is dependent on a source of energy from light.

The term "microorganism" is intended to mean any living unicellular organism belonging to one of the following kingdoms: monera, protists, mycetes or protozoa, having a eukaryotic or prokaryotic cellular structure, of microscopic or ultramicroscopic size, and having a metabolic and reproductive potential. Said unicellular microorganisms may be involved in the formation of filaments or biofilms.

Preferably, the photosynthetic microorganisms according to the invention are eukaryotic microalgae, more preferably Chlorophyceae of the *Chlorella* genus, or prokaryotic microalgae such as cyanobacteria, preferably of the *Spirulina* or *Arthrospira* genus (spirulin). The latter are well known to those skilled in the art for being used as food supplements, in particular in developing countries.

The term "organic selenium" is intended to mean a collection of molecules containing at least one compound having at least one selenium atom in its chemical structure, capable of being produced by a living organism, such as, in particular, the amino acids selenomethionine, methylselenocysteine and selenocysteine, or peptides or proteins containing them.

The photosynthetic microorganisms thus enriched in selenium can be used as such, or else as a food additive. They can, for example, be dehydrated so as to form a stable powder that can be incorporated into compositions acting as a base for the preparation of transformed products, but can also be used live as probiotics in food product transformation processes, for the purpose of obtaining, for example, fermented milks or drinks.

A subject of the present invention is therefore a novel method for enriching a photosynthetic microorganism in selenomethionine and/or in selenocysteine, characterized in that said photosynthetic microorganism is cultured in a culture medium comprising a compound of selenohydroxy acid type.

Preferably, the compound of selenohydroxy acid type is a compound of general formula (I), or a precursor, a salt or alternatively an ester or amide derivative thereof:

(I)

in which formula:

n is equal to 0, 1 or 2;

$R_1$ is an OH, $OCOR_3$, $OPO_3H_2$, $OPO_3R_4R_5$ or $OR_6$ group;

$R_2$ is an OH, $R_3$, $NHR_7$, S-cysteinyl or S-glutathionyl group; it being understood that, when n=1 and $R_2$ is OH, then $R_1$ cannot be OH;

$R_3$ is an alkoxyl, ceramide 1, ceramide 2, ceramide 3, ceramide 4, ceramide 5, ceramide 6a and 6b, S-cysteinyl or S-glutathionyl group, or a group chosen from the following:

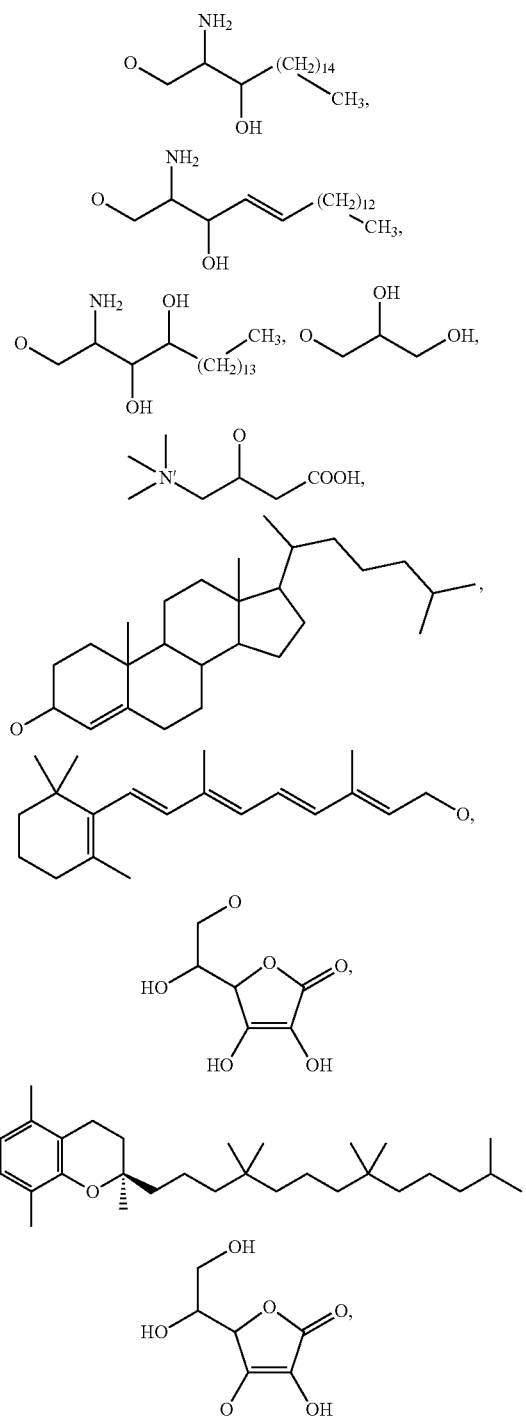

-continued

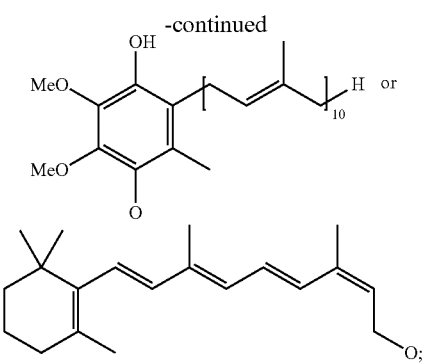

or

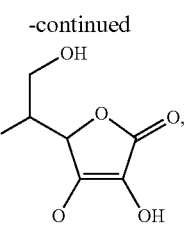

Preferably, $R_3$ is an alkoxyl, S-cysteinyl or S-glutathionyl group;

$OR_4$ is a $(C_1-C_{26})$ alkoxyl, ceramide 1, ceramide 2, ceramide 3, ceramide 4, ceramide 5 or ceramide 6a and 6b group, or a group chosen from the following:

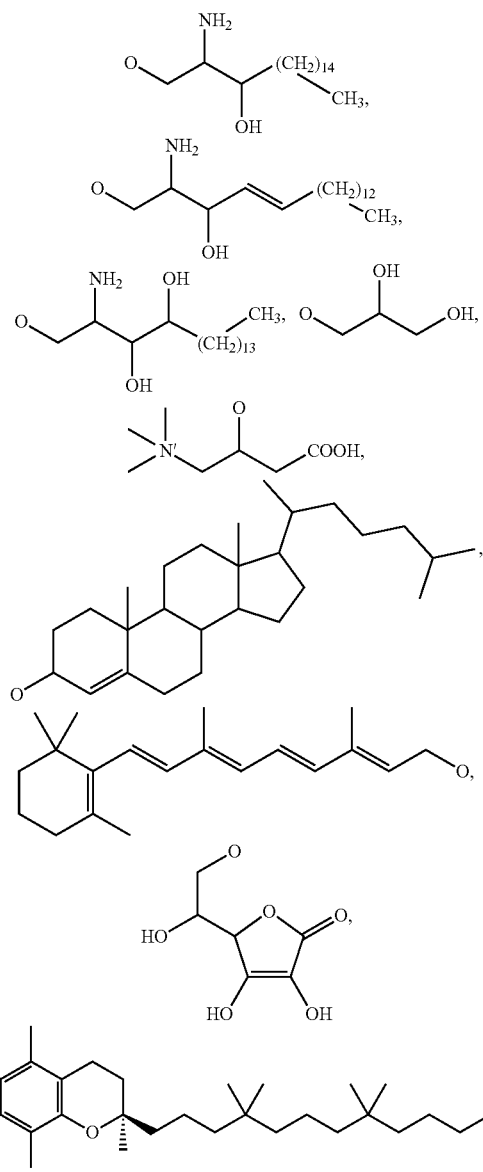

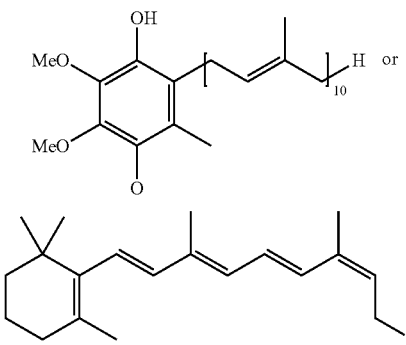

or

Preferably, $OR_4$ is a $(C_1-C_{26})$ alkoxyl group;

$OR_5$ is a $(C_1-C_{26})$ alkoxyl, ceramide 1, ceramide 2, ceramide 3, ceramide 4, ceramide 5 or ceramide 6a and 6b group, or a group chosen from the following groups:

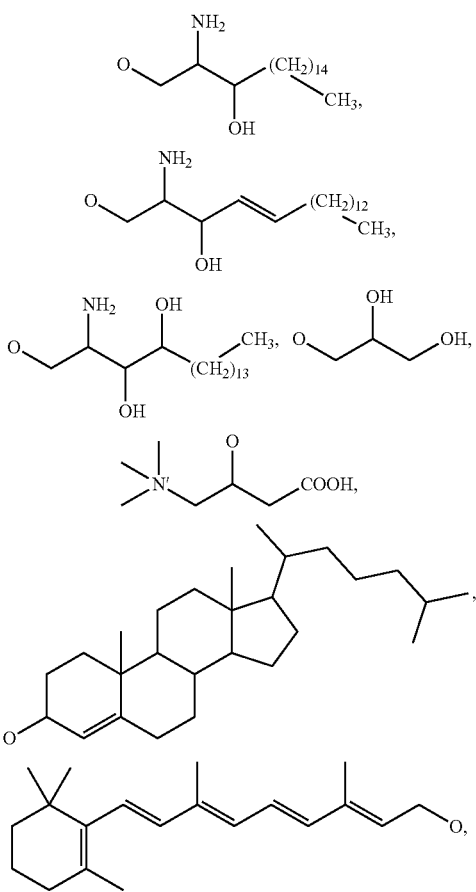

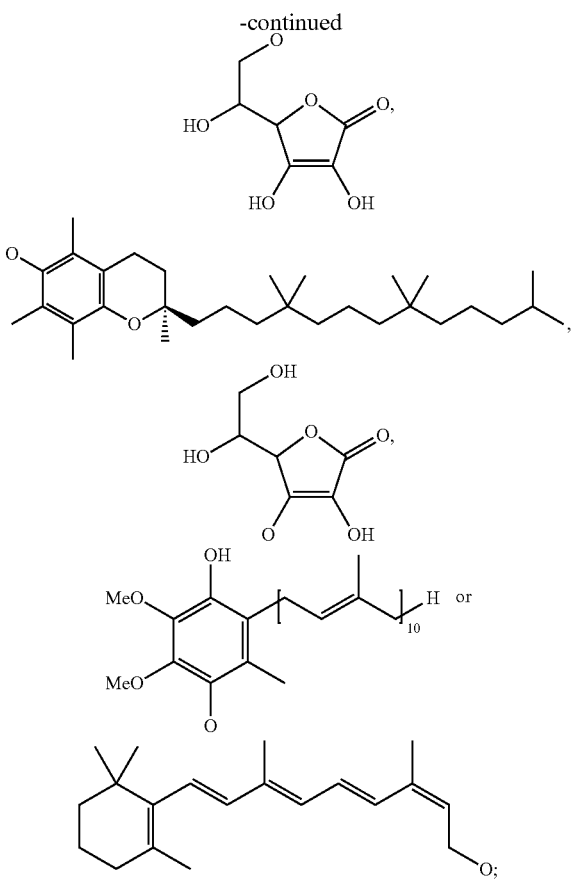

Preferably, $OR_5$ is a ($C_1$-$C_{26}$) alkoxyl group;

$OR_6$ is a pyruvate, lactate, citrate, fumarate, maleate, myristate, palmitate, stearate, palmitoleate, oleate or linoleate group, a natural fatty acids group or a 13-cis-retinoate group;

$R_7$ is an H or ($C_1$-$C_{26}$) alkyl group, a natural amino acid or a natural amine.

In formula (I) above:

the term "alkyl" is intended to mean a linear or cyclic, optionally branched, optionally fluorinated or polyfluorinated, group containing 1 to 26 carbon atoms, and optionally comprising one or more carbon-carbon double bonds, such as, for example, methyl, ethyl, isopropyl, trifluoromethyl, linoleyl, linolenyl or palmitoyl;

the term "alkoxyl" is intended to mean a linear or cyclic, optionally branched, optionally fluorinated or polyfluorinated, group derived from a primary, secondary or tertiary alcohol containing 1 to 26 carbon atoms, and optionally comprising one or more carbon-carbon double bonds, such as, for example, methoxyl, ethoxyl, isopropoxyl, trifluoromethoxyl, linoleoxyl, linolenoxyl or palmitoxyl;

structures of radicals of ceramide type are described in particular in "Cosmetic Lipids and the Skin Barrier", Thomas Förster Ed. 2002, Marcel Dekker, Inc., p 2, FIG. 2;

the term "natural" is intended to mean any corresponding compound found in the metabolism of organisms of the plant and animal world, and also in that of humans (Steglich W., Römpp Encyclopedia Natural Products, G. Thieme ed.);

the term "oligomer" is intended to mean any compound formed by the linking of 2 to 15 monomers connected to one another by means of an ester-type bond;

the term "polymer" is intended to mean any compound formed by the linking of more than 15 monomers connected to one another by means of an ester-type bond.

According to the invention, said compounds of formula (I) are preferably used in the form of calcium salts, zinc salts or magnesium salts, which generally makes it possible to obtain better solubility in culture media, and also better assimilation by the photosynthetic microorganisms.

In one preferred embodiment of the invention, the photosynthetic microorganism is chosen from the group formed by Cyanophyceae and Chlorophyceae. Thus, the photosynthetic microorganism is advantageously selected from Cyanophyceae or Chlorophyceae, preferably chosen from the group formed by Chlorophyceae of the *Chlorella* genus and Cyanophyceae of the *Spirulina* or *Arthrospira* genus.

The invention relates more particularly to the use of a compound of formula (I), chosen (or taken) from L-2-hydroxy-4-methylselenobutanoic acid,
D-2-hydroxy-4-methylselenobutanoic acid,
DL-2-hydroxy-4-methylselenobutanoic acid,
or a salt of these compounds.

These compounds are described in application WO 2006/008190.

A subject of the invention is also a photosynthetic microorganism enriched in organic selenium, that can be obtained according to the method of the invention. Such a microorganism generally has an organic selenium content of greater than 500 ppm, preferably greater than 1000 ppm, more preferably greater than 2000 ppm on a selenium equivalent basis, and an inorganic selenium content of less than 0.5%, preferably less than 0.2%, and more preferably less than 0.1% by dry weight of said microorganism. Preferably, the invention relates to the case where the photosynthetic microorganism comprises less than 1.5%, preferably less than 0.5%, more preferably less than 0.1% by mass of inorganic selenium relative to the total selenium.

In other words, the residues of selenium in inorganic form that are present in the photosynthetic microorganisms enriched according to the method of the invention generally account for less than 1.5% of the total selenium present in the microorganisms, which generally represents less than 0.5% of the total dry biomass (dry weight) of said microorganism.

The invention relates most particularly to a photo-synthetic microorganism enriched in organic selenium, characterized in that the content, of said microorganism, of selenium in the form of selenomethionine represents more than 50%, preferably more than 70%, more preferably more than 80%, and even more preferably more than 90%, by mass of selenium, relative to the total selenium present in said photosynthetic microorganism. Such a proportion of selenomethionine represents a considerable and particularly advantageous improvement, in terms of amount and quality of organic selenium present in the microorganism, compared with what was obtained in the prior art.

In particular, the invention relates to the case where the microorganism is characterized in that it is a selenium-enriched Chlorophycea microalga, preferably of the *Chlorella* genus, and in that said microorganism contains a selenomethionine content of generally greater than 50 micrograms of selenium equivalent per gram (μgSe/g), preferably greater than 70 μgSe/g, and more preferably greater than 100 μgSe/g by dry weight of said microorganism.

The amount of selenium fixed inside the microorganisms in the form of organic molecules (selenomethionine, selenocysteine, or the like) or inorganic molecules (selenium salts) is expressed as mass of selenium per gram (μgSe/g) of dry weight of the microorganisms. In other words, the selenium content of the photosynthetic microorganisms is established by calculating the mass of selenium present in these organic or inorganic molecules, related back to the total dry biomass of the microorganism. In addition, the proportions by mass of selenium present in organic and inorganic form are also established and expressed as percentages relative to the mass of total selenium.

The content of total selenium and selenium in the form of selenomethionine, of the photosynthetic microorganisms according to the invention, can be determined, respectively, by mineralization and enzyme digestion after centrifugation and lyophilization of the microorganisms, for example by following the method according to Lobinsky et al., described in Mester, Z. et al. (2006) Annal. Bioanal. Chem. 385:168-180.

The results obtained according to the present invention, which are illustrated in the examples of the present application, show that the photosynthetic microorganisms, more particularly the Chlorophycea and Cyanophycea microalgae accumulate selenium in the form of selenomethionine in a content of generally greater than 100 micrograms of selenium equivalent per gram (μgSe/g), preferably greater than 200 μgSe/g, more preferably greater than 500 μgSe/g, even more preferably greater than 1000 μgSe/g by dry weight, and even greater than 1400 μgSe/g by dry weight of these microalgae.

The invention therefore relates more particularly to a Chlorophycea or a Cyanophycea enriched in organic selenium, characterized in that its content of organic selenium in the form of selenomethionine is generally greater than 100 μgSe/g, preferably greater than 200 μgSe/g, more preferably greater than 500 μgSe/g, and even more preferably greater than 1000 μgSe/g by dry weight.

Such a Chlorophycea or Cyanophycea enriched in organic selenium is generally characterized in that its content of organic selenium in the form of selenomethionine represents more than 50%, preferably more than 70%, more preferably more than 80%, even more preferably more than 90%, and even more than 95% of the total selenium that it contains, and also in that its residual content of inorganic selenium, generally less than 1.5%, is preferably less than 0.5%, more preferably less than 0.1% of the total selenium that it contains. In general, its residual content of inorganic selenium is less than 1%, preferably less than 0.5%, more preferably less than 0.2%, and even more preferably less than 0.1% of the total biomass of said Chlorophycea, by dry weight.

The invention also relates to the production of food, cosmetic or pharmaceutical products from said photosynthetic microorganisms enriched in selenium according to the method of the present invention. This production makes use of techniques known to those skilled in the art.

The photosynthetic microorganisms according to the invention can also be of use in animal nutrition, in particular for the purpose of obtaining secondary derivatives enriched in organic selenium, for instance fish, milk or eggs.

The derived products and molecules thus obtained are of use in various applications, including those summarized in the preamble, in particular as a cosmetic, pharmaceutical or nutritional agent.

A subject of the invention is also the use of a selenium-enriched photosynthetic microorganism according to the invention, as a cosmetic, pharmaceutical (or therapeutic) or nutritional product (or agent).

The invention also relates to the compositions, generally cosmetic, pharmaceutical or nutritional compositions, comprising said photosynthetic microorganisms.

The invention also relates to a culture medium for a photosynthetic microorganism, characterized in that it comprises one or more of the compounds of formula (I) defined above.

Such a culture medium is of use for implementing the method of enriching photosynthetic microorganisms in selenium according to the invention.

In particular, the invention relates to a solid or liquid culture medium comprising at least one compound of formula (I), preferably 2-hydroxy-4-methylselenobutanoic acid or a salt thereof, at a concentration of between 0.5 and 2000 mg/l, preferably between 1 and 1000 mg/l, more preferably between 2 and 500 mg/l, i.e. respectively approximately between 0.2 and 800 mg/l of said compound on a selenium equivalent basis, preferably between 0.4 and 400 mg/l of said compound on a selenium equivalent basis, more preferably between 0.8 and 200 mg/l of said compound on a selenium equivalent basis.

For the microalgae of marine origin, the compounds of formula (I) can be diluted in sterile filtered seawater or in synthetic seawater produced, for example, from the "Reef Crystal" medium from the company Aquarium Systems Inc., so as to form a minimum culture medium.

A method for preparing microalgae according to the invention can in particular comprise one or more of the following steps:
preparing a culture medium, preferably a minimum medium, containing the chemical elements necessary for the growth of a microalga;
introducing, into the culture medium, a compound of formula (I), preferably 2-hydroxy-4-methylselenobutanoic acid, as organic source of selenium;
adjusting the pH of the mixture to a value of between 6 and 10;
placing an inoculum of preculture of said microalga in culture in the mixture thus formed, at a temperature of between 12 and 45° C., with orbital shaking of between 100 and 500 rpm, and an atmosphere that may contain from 0 to 20% of oxygen and from 0.3% to 20% of carbon dioxide, preferably from 24 to 120 hours;
centrifuging the mixture at between 4000 and 10 000 rpm for a few minutes, or filtering the mixture through a 0.2 micrometer filter and rinsing the filter through with physiological saline;
taking the cell pellet up in physiological saline;
centrifuging again at between 4000 and 10 000 rpm for a few minutes;
recovering the moist cell pellet which contains the selenium-enriched microalgae.

The moist cell pellet may be lyophilized or air-dried.

Other characteristics and advantages of the invention are given in the examples which follow. The examples hereinafter are provided only by way of illustration and cannot in any way limit the scope of the invention.

EXAMPLES

Example 1

Production of the *Chlorella vulgaris* microalga enriched in selenium in a medium containing 2-hydroxy-4-methylselenobutanoic acid (THD-177), under autotrophic conditions Experimental Conditions The strain used under photoautotrophic conditions is *Chlorella vulgaris* SAG211-11B: an axenic strain originating from the SAG collection of the University of Göttingen (SAG: Sammlung von Algenkulturen der Universität Göttingen [Collection of Alga Cultures of the University of Göttingen]).

This strain was cultured in the BG-11 medium (blue-green medium) described by [Stanley R Y et al. 1971 Bacteriol. Rev. 35:171-205], the composition of which is the following (per liter):

(1) $NaNO_3$: 1.5 g
(2) $K_2HPO_4$: 0.04 g
(3) $MgSO_4.7H_2O$: 0.075 g
(4) $CaCl_2.2H_2O$: 0.036 g
(5) Citric acid: 0.006 g
(6) Ferric ammonium citrate: 0.006 g
(7) EDTA-$Na_2$: 0.001 g
(8) $Na_2CO_3$: 0.02 g
(9) Distilled water 1.0 l
(10) Solution of trace elements: 1 ml/l
    $H_3BO_3$: 2.86 g
    $MnCl_2.4H_2O$: 1.81 g
    $ZnSO_4.7H_2O$: 0.222 g
    $Na_2MoO_4.2H_2$: 0.39 g
    $CuSO_4.5H_2O$: 0.08 g
    $Co(NO_3)_2.6H_2O$: 0.05 g The pH was adjusted to 7.1 and the medium was autoclaved at 121° C. for 15 minutes.

This strain was cultured at 25° C., 2400+/−200 Lux under photoautotrophic conditions for 2 to 7 days with orbital shaking (80 rpm), $OD_{init660nm}$=0.05. The $OD_{660nm}$ of the strain reaches 0.5 in 48 h.

Culture Conditions

The organic source of selenium, namely 2-hydroxy-4-methylselenobutanoic acid (THD-177, Tetrahedron SAS, France, CAS: 873660-49-2) was administered at a concentration of between 0.5 mg/l and 100 mg/l on a selenium equivalent basis, i.e., respectively, 1.25 mg/l and 250 mg/l of 2-hydroxy-4-methylselenobutanoic acid. The compound containing selenium was added just one time (i.e. an amount of between 0.125 mg and 25 mg per 100 ml of culture) at the beginning of the culture, or several times at regular time intervals, the duration of the intervals being between 6 and 24 hours, the culture having been maintained for a period of 2 to 7 days.

Example 2

Production of the *Chlorella vulgaris* microalga enriched in selenium in a medium containing 2-hydroxy-4-methylselenobutanoic acid (THD-177) (example according to the invention) or in a medium containing sodium selenite (comparative example) under mixotrophic conditions (presence of light and of carbohydrate—glucose—in the medium)

In these tests, the strain used is a strain of *Chlorella vulgaris* SAG211-11B: an axenic strain originating from the SAG collection of the University of Göttingen (SAG: Sammlung von Algenkulturen der Universität Göttingen [Collection of Alga Cultures of the University of Göttingen]) which was cultured under mixotrophic conditions in the following medium:

| | |
|---|---|
| Yeast extracts | 0.33 g |
| Beef extracts | 0.33 g |
| Tryptose | 0.66 g |
| $FeSO_4$ | 0.66 mg |
| Glucose | 3.3 g |
| Distilled water | qs 1.0 l |

The pH was adjusted to 7.2 and the medium was autoclaved at 121° C. for 15 minutes.

The organic source of selenium, namely 2-hydroxy-4-methylselenobutanoic acid (THD-177, Tetrahedron SAS, France, CAS: 873660-49-2) was administered at a concentration of 20 mg/l on a selenium equivalent basis, i.e. 50 mg/l of 2-hydroxy-4-methylselenobutanoic acid.

The inorganic selenium source (NaSe, sodium selenite) was administered at a concentration of 20 mg/l on a selenium equivalent basis, i.e. 43.9 mg/l of sodium selenite.

The compound containing selenium was added just one time in the exponential growth phase of the *Chlorella vulgaris* strain (i.e. 3 days after the inoculation).

Preparation of the Samples for Analyses:

After incubation for 7 days, the medium was filtered through a 0.2 micron Nalgene membrane (Ref a-PES, diameter 90 mm), and the cell retentate was rinsed with physiological saline. The wet cell mass was lyophilized for analysis of the constituents containing selenium (total selenium, selenomethionine and sodium selenite).

Analysis of the Constituents Containing Selenium of *Chlorella vulgaris*

The total selenium was assayed by ICP coupled to detection by mass, after mineralization of the sample. The speciation of the selenium was carried out by high performance liquid chromatography coupled to tandem mass detection, after enzyme digestion of the sample, according to the method described by Lobinsky et al., in Mester, Z. et al. (2006) *Annal. Bioanal. Chem.* 385: 168-180.

Results

Table 1 below indicates the average values, on a selenium equivalent basis, obtained in triplicate for incubation times of 7 days.

TABLE 1

Analysis of the components containing selenium of the *Chlorella vulgaris* microalga

| | Total Se mgSe/kg biomass | SeMethionine mgSe/kg biomass | Se(IV) mgSe/kg biomass |
|---|---|---|---|
| Addition THD177 20 mgSe/l | 1293 ± 23 | 1274 ± 109 (98.5% of total Se) | 6 ± 1 (0.4% of total Se) |
| Addition NaSe 20 mgSe/l | 144 ± 5 | 29 ± 2 (20% of total Se) | 4.1 ± 0.4 (2.7% of total Se) |

The results obtained showed, for the same dose of selenium added in the form of THD177 or of NaSe, in this case 20 mgSe/l, that:
- nine times more total Se was detected if the addition is carried out in the form of THD177 than if the addition is carried out in the form of NaSe;
- the level of selenium accumulated intracellularly in the form of selenomethionine, obtained by means of an addition of THD177, is 44 times higher than that obtained by means of an addition in the form of NaSe;
- the level of selenium accumulated intracellularly in the form of selenomethionine reaches virtually 100% (98.5%) of the intracellular compound forms containing selenium if the addition is carried out in the form of THD177, compared with a level of 20% with NaSe; and that:

only 0.4% of Se(IV) in the total selenium was detected if the addition is THD177, whereas 2.7% of Se(IV) were detected in the total selenium in the case of the addition of NaSe.

Example 3

Production of the *Arthrospira platensis* microalga enriched in selenium in a medium containing 2-hydroxy-4-methylselenobutanoic acid (THD-177) (example according to the invention) or in a medium containing sodium selenite (comparative example) under autotrophic conditions In these tests, the strain used is a strain of *Arthrospira platensis* 3054-E0001.

The 3054-50001 strain was cultured under autotrophic conditions in the following medium:

| | |
|---|---|
| Yeast extracts | 0.33 g |
| Beef extracts | 0.33 g |
| Tryptose | 0.66 g |
| FeSO$_4$ | 0.66 mg |
| Distilled water | qs 1.0 l |

The pH was adjusted to 7.2 and the medium was autoclaved at 121° C. for 15 minutes.

The organic source of selenium, namely 2-hydroxy-4-methylselenobutanoic acid (THD-177, Tetrahedron SAS, France, CAS: 873660-49-2) was administered at a concentration of 25 mg/l on a selenium equivalent basis, i.e. 62.5 mg/l of 2-hydroxy-4-methylselenobutanoic acid.

The inorganic selenium source (NaSe, sodium selenite) was administered at a concentration of 25 mg/l on a selenium equivalent basis, i.e. 54.4 mg/l of sodium selenite.

The compound containing selenium was added just one time, just after the inoculation with the *Arthrospira platensis* strain (i.e. T=0).

Preparation of the Samples for Analyses:

After incubation for 10 days, the cell pellet was filtered through a 0.2 micron Nalgene membrane, and the cell retentate was rinsed with physiological saline. The wet cell mass was lyophilized for analysis of the constituents containing selenium (total selenium, selenomethionine and sodium selenite).

Analysis of the Constituents Containing Selenium of *Arthrospira platensis*

The total selenium was assayed by ICP coupled to detection by mass, after mineralization of the sample. The speciation of the selenium was carried out by high performance liquid chromatography coupled to tandem mass detection, after enzyme digestion of the sample, according to the method described by Lobinsky et al., in Mester, Z. et al. (2006) *Annal. Bioanal. Chem.* 385: 168-180.

Results

Table 2 below indicates the average values, on a selenium equivalent basis, obtained in triplicate for incubation times of 10 days.

TABLE 2

Analysis of the components containing selenium of the *Arthrospira platensis* microalga

| | Total Se mgSe/kg biomass | SeMethionine mgSe/kg biomass | Se (IV) mgSe/kg biomass |
|---|---|---|---|
| Addition THD177 25 mgSe/l | 1431 ± 68 | 1402 ± 47 (98% of total Se) | 17.2 ± 0.7 (1.2% of total Se) |
| Addition NaSe 25 mgSe/l | 177 ± 2 | 13 ± 3 (7% of total Se) | 5.1 ± 0.3 (2.9% of total Se) |

The results obtained showed, for the same dose of selenium added in the form of THD177 or of NaSe added, in this case 25 mgSe/l, that:

eight times more total Se was detected for an addition carried out in the form of THD177 than for an addition carried out in the form of NaSe;

the level of selenium accumulated intracellularly in the form of selenomethionine, obtained by means of an addition of THD177, is 108 times higher than that obtained by means of an addition in the form of NaSe;

the level of selenium accumulated intracellularly in the form of selenomethionine reaches 98% of the intracellular compound forms containing selenium if the addition is carried out in the form of THD177, compared with a level of 7% with NaSe; and that:

only 1.2% of Se(IV) in the total selenium was detected if the addition is THD177, whereas 2.9% of Se(IV) were detected in the total selenium in the case of the addition of NaSe.

Example 4

Production of the *Arthrospira platensis* micro-alga enriched in selenium in a medium containing 2-hydroxy-4-methylselenobutanoic acid (THD-177) (example according to the invention)

In these tests, the strain used is a strain of *Arthrospira platensis* 3054-E0001. A comparison is made between the results of the previous example, example 3, during which the addition, according to the invention, of the compound containing selenium THD-177 was carried out just one time just after the inoculation with the *Arthrospira platensis* strain, and a new experiment in which the addition, according to the invention, of the compound containing selenium THD-177 was carried out in the exponential phase of culture of said *Arthrospira platensis* strain, as in example 2.

Results

Table 3 below indicates the average values, on a selenium equivalent basis, obtained in triplicate for incubation times of 10 days.

TABLE 3

Analysis of the components containing selenium
of the *Athrospira platensis* microalga
Analysis of the components containing selenium
of the *Arthrospira platensis* microalga

| | Total Se mgSe/kg biomass | SeMethionine mgSe/kg biomass | THD177 mgSe/kg biomass | Se(IV) mgSe/kg biomass |
|---|---|---|---|---|
| Addition at inoculation THD177 25 mgSe/l | 1431 ± 68 | 1402 ± 47 (98% of total Se) | 5 ± 1 (0.35% of total Se) | 17.2 ± 0.7 (1.2% of total Se) |
| Addition exponential phase THD177 25 mgSe/l | 1274 ± 16 | 1078 ± 89 (85% of total Se) | 11 ± 2 (0.86% of total Se) | 14 ± 2 (1.1% of total Se) |

The results showed that 12% more total selenium and 30% more selenium in the form of selenomethionine were obtained in the "addition at T0" test compared with the "addition in the exponential phase" test. This difference could be the result of the longer contact time between the biomass and the THD177 in the "addition at T0" test than in the other, "addition in the exponential phase", test.

In both cases, the intracellular Se(IV) level remains low at 1% of total selenium.

The invention claimed is:

1. A photosynthetic microorganism enriched in organic selenium, wherein the content of selenium in the form of selenomethionine in said microorganism represents more than 50% by mass of selenium, relative to the total selenium present in said photosynthetic microorganism.

2. The photosynthetic microorganism enriched in organic selenium according to claim 1, wherein the photosynthetic microorganism comprises less than 1.5% by mass of inorganic selenium relative to the total selenium.

3. The photosynthetic microorganism enriched in organic selenium according to claim 1, wherein said microorganism comprises less than 1.5% by mass of inorganic selenium relative to the total dry weight of said microorganism.

4. The photosynthetic microorganism enriched in organic selenium of claim 1 which is a Chlorophyceae.

5. The Chlorophyceae enriched in organic selenium of claim 4, wherein its content of organic selenium in the form of selenomethionine is greater than 1000 ug Se/g by dry weight.

6. The Chlorophyceae enriched in organic selenium according to claim 4, wherein its residual content of inorganic selenium is less than 2% by mass, relative to the total selenium that it contains.

7. The Chlorophyceae enriched in organic selenium according to claim 5, wherein its residual content of inorganic selenium becomes established at less than 2%, by mass of inorganic selenium, relative to the total biomass of said *Chlorophyceae*, by dry weight.

8. The photosynthetic microorganism enriched in organic selenium of claim 1 which is a Cyanophyceae.

9. The Cyanophyceae enriched in organic selenium of claim 8, wherein its content of organic selenium in the form of selenomethionine is greater than 1000 µg Se/g by dry weight.

10. The Cyanophyceae enriched in organic selenium according to claim 8, wherein its residual content of inorganic selenium is less than 2% by mass, relative to the total selenium that it contains.

11. The Cyanophyceae according to claim 8, which belongs to the *Spirulina* or *Arthrospira* genus.

12. In a method of using a photosynthetic microorganism as a cosmetic, pharmaceutical or nutritional agent, the improvement wherein the photosynthetic microorganism is a photosynthetic microorganism enriched in organic selenium according to claim 1.

13. A composition comprising at least one photosynthetic microorganism enriched in organic selenium according to claim 1.

14. The composition according to claim 13, wherein said composition is a cosmetic, pharmaceutical or nutritional composition.

15. The photosynthetic microorganism enriched in organic selenium of claim 1 which belongs to the *Chlorella* genus.

16. The *Chlorella* enriched in organic selenium of claim 15, which is *Chlorella vulgaris*.

17. The *Chlorella* enriched in organic selenium of claim 15, wherein its content of organic selenium in the form of selenomethionine is greater than 1000 ug Se/g by dry weight.

18. The *Chlorella* enriched in organic selenium of claim 15, wherein its residual content of inorganic selenium is less than 2% by mass, relative to the total selenium that it contains.

19. The *Chlorella* enriched in organic selenium of claim 17, wherein its residual content of inorganic selenium becomes established at less than 2%, by mass of inorganic selenium, relative to the total biomass of said *Chlorella*, by dry weight.

20. A method for enriching the photosynthetic microorganism of claim 1 in organic selenium, comprising culturing the photosynthetic microorganism in a medium comprising a selenohydroxy acid compound of formula (I)

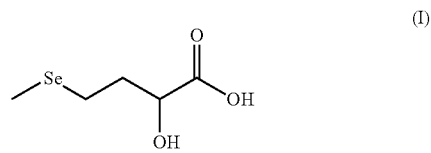

or a salt thereof.

21. The method according to claim 20, wherein said compound of formula (I) is chosen from:
- L-2-hydroxy-4-methylselenobutanoic acid,
- D-2-hydroxy-4-methylselenobutanoic acid,
- DL-2-hydroxy-4-methylselenobutanoic acid, or a salt thereof.

22. The method according to claim 21, wherein said compound of formula (I) is in the form of a calcium salt, a zinc salt or a magnesium salt.

23. The method according to claim 20, wherein the photosynthetic microorganism is selected from the group consisting of Cyanophyceae and Chlorophyceae.

24. The method according to claim 20, wherein the photosynthetic microorganism belongs to the *Chlorella* genus.

* * * * *